United States Patent [19]

London

[11] Patent Number: 5,202,113
[45] Date of Patent: Apr. 13, 1993

[54] PLAQUE-INHIBITING PROTEIN FROM BACTEROIDES LOESCHEI AND METHODS FOR USING THE SAME

[75] Inventor: Jack London, Rockville, Md.

[73] Assignee: The United States of America as represented by the Department of Health and Human Services, Washington, D.C.

[21] Appl. No.: 516,463

[22] Filed: Apr. 30, 1990

[51] Int. Cl.$^5$ ............................. A61K 37/02; A61K 7/16
[52] U.S. Cl. .................................. 424/54; 424/49; 424/50; 424/92; 424/88; 530/324; 530/395; 530/825; 514/900; 514/901; 514/902; 514/12; 514/21

[58] Field of Search ................ 424/48, 49, 50, 92, 424/88, 54; 530/324, 395, 825; 514/900–902

[56] References Cited

U.S. PATENT DOCUMENTS

| | | | |
|---|---|---|---|
| 4,659,561 | 4/1987 | Fives-Taylor | 424/50 |
| 4,746,512 | 5/1988 | Kawai et al. | 424/49 |
| 4,789,735 | 12/1988 | Frank | 530/395 |
| 4,795,803 | 1/1989 | Lindberg et al. | 424/92 |

OTHER PUBLICATIONS

Fachon-Kalweit et al., *Infection and Immunity*, 48(3), 617–624 (1985).

Weiss et al., *Infection and Immunity*, 56(1), 219–244 (1988).

London et al., *Infection and Immunity*, 57(12), 3940–3944, Dec. 1989.

Weiss et al., "Fimbria-Associated Proteins ...", *J. of Bacteriology*, Sep. 1987, pp. 4215–4222.

Weiss et al., "Characterization of Monoclonal Antibodies ...", *Infection and Immunity*, Jan. 1988, pp. 219–224.

Weiss et al., "Localization and Enumeration of Fimbria-Associated Adhesions ...", *J. of Bacteriology*, Mar. 1988, pp. 1123–1128.

Hanson et al., "Purification of the *Escherichia coli* Type 1 Pilin ...", *J. of Bacteriology*, Aug. 1988, pp. 3350–3358.

Hoschutzky et al., "Isolation and Characterization of the ...", *Infection and Immunity*, Jan. 1989, pp. 76–81.

*Primary Examiner*—F. T. Moezie
*Attorney, Agent, or Firm*—Birch, Stewart, Kolasch & Birch

[57] ABSTRACT

A purified, characterized surface protein from *Bacteroides loeschei* is an adhesin which is useful in inhibiting plaque formation. The adhesin is also useful in a diagnostic assay for gingivitis, a diagnostic indicator for changes in the surface components of certain human tissues, and as a binding agent to purify polysaccharides.

6 Claims, 6 Drawing Sheets

A    B    C    D

A    B

B.I.  A Y C H V K N A T G E D I E R I K E E D V D D D I E V D
Padh  V D N L T F R K L I P A C T V S N T T V D W Q D V E I
TI    F A X X K T A D G I A I P I G G G X A D V Y V D L A P V V

PLAQUE-INHIBITING PROTEIN FROM BACTEROIDES LOESCHEI AND METHODS FOR USING THE SAME

BACKGROUND OF THE INVENTION

1. Field of the Invention

The present invention relates to a surface protein from *Bacteroides loeschei* which is an adhesin useful in preventing plaque formation in the oral cavity. More specifically, the present invention relates to a purified, characterized adhesin isolated from *B. loeschei* and its use in a method for preventing or retarding the formation of plaque in the oral cavity as well as other uses based on the binding capabilities of the adhesin.

2. Description of Related Art

The present technologies used to clear microorganisms from the oral cavity rely on non-specific agents to disrupt prior colonization and plaque formation. These agents also pertubate the normal flora which actually protect the hard surfaces in the oral cavity. Such agents include toothpastes, mouthwashes, chewing gum, etc., which all work in a non-specific manner, primarily by means of detergents and abrasives. Thus, it is desirable to obtain a better means for clearing specific unwanted microorganisms from the oral cavity so as to avoid pertubating the normal flora.

Most bacteria isolated from the human oral cavity possess the ability to participate in intergeneric coaggregation, i.e. bacteria from different genera bind to each other primarily via a protein on one attaching to a saccharide component on the other. Coaggregation is characterized by a highly specific binding between stable surface components found on two different bacterial types. Intergeneric coaggregation is thought to play an important role in the formation of dental plaque deposits. *Streptococcus sanguis* is one of the earliest colonizers of the clean tooth surface and is found in significant numbers in dental plaque. Other primary colonizers of oral hard tissue and the soft tissues of the host (i.e. neuraminidase treated erythrocytes and epithelial cells) include *S. oralis* and *Gamella morbillorum*.

*Bacteroides loeschei* PK1295, a human oral isolate, synthesizes an adhesin which mediates its coaggregation with *S. sanguis* 34 (Weiss et al, "Fimbria-associated proteins of *Bacteroides loeschei* PK1295 mediate intergeneric coaggregations," *J. Bacteriol.*, 169, pp. 4215–4222 (1987)) and hemagglutination of a variety of neuraminidase-treated mammalian erythrocytes (Weiss et al, "Fimbria-associated adhesin of *Bacteroides loeschei* that recognizes receptors on procaryotic and eucaryotic cells," *Infect. Immun.* 57, pp. 2912–2913 (1989)). Adhesin-specific monoclonal antibodies (MAb) prepared by immunizing mice with adhesin-bearing fimbriae were screened for inhibition of coaggregation (Weiss et al, "Characterization of monoclonal antibodies to fimbria-associated adhesins of *Bacteroides loeschei* PK1295," *Infect. Immun.*, 56, pp. 219–224 (1988)). Subsequently, the MAbs were used to estimate the number of adhesin molecules per cell and immunoelectron microscopy revealed that the adhesins were associated with the distal portion of the microorganisms fimbriae (Weiss et al, "Localization and enumeration of fimbria-associated adhesins of *Bacteroides loeschei*," *J. Bacteriol.*, 170, pp. 1123–1128 (1988)). Although some of the coaggregation properties of adhesins from *B. loeschei* are known, a substantially purified and characterized adhesin has heretofore not been prepared.

SUMMARY OF THE INVENTION

Therefore, it is an object of the present invention to provide a purified, characterized adhesin isolated from *Bacteroides loeschei* which exhibits plaque-inhibiting properties in a specific manner without disturbing the normal flora in the oral cavity.

It is a further object of the present invention to provide a method for inhibiting plaque formation in the oral cavity by applying a composition containing the adhesin to plaque-prone areas of the teeth or gingivae in the oral cavity.

Another object of the present invention is to provide an oral composition, such as a dentifris, mouthwash or toothpaste, for applying the plaque-inhibiting adhesin to the oral cavity.

Still a further object of the present invention is to provide a diagnostic assay for gingivitis wherein antibodies prepared against the adhesin are used as a diagnostic aid to detect the presence of *B. loeschei* in plaque or saliva.

It is still a further object of the present invention to employ the adhesin isolated from *B. loeschei* as a binding agent for use a diagnostic indicator for changes in the surface components of certain human tissues.

It is yet a further object of the present invention to provide a method of using the adhesin isolated from *B. loeschei* as a binding agent to purify polysaccharides.

The foregoing objects and others are accomplished in accordance with the present invention, generally speaking, by providing a purified, characterized surface protein isolated from *Bacteroides loeschei* which exhibits plaque-inhibiting properties. The present invention further encompasses a method for inhibiting plaque formation by the application of the adhesin in an appropriate composition to the oral cavity, as well as the oral composition which includes the adhesin. The present invention also encompasses providing a diagnostic assay for gingivitis using antibodies prepared against the adhesin; employing the adhesin as a diagnostic indicator for changes in the surface components of certain human tissues; and providing a method for using the adhesin as a binding agent to purify polysaccharides.

Further scope of the applicability of the present invention will become apparent from the detailed description and drawings provided below. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The invention is further illustrated in the accompanying drawings wherein:

FIG. 9 is a comparison of the N-terminal amino acid sequences of *E. coli* type 1 and P adhesin and *B. loeschei* (B. 1) adhesin.

DETAILED DESCRIPTION OF THE INVENTION

Figure 1:
FIG. 1 shows the results of an immunoblot analysis demonstrating the purity of the streptococcal-specific adhesin.

The purified, characterized surface protein from *Bacteroides loeschei* in accordance with the present invention is an adhesin which mediates the organism's attachment to bacteria which are primary colonizers of oral hard and soft tissues. *B. loeschei* is a gram negative bacterium found in the oral cavity. Primary colonizers of oral hard tissue and soft tissues of the host (i.e. neuraminidase treated erythrocytes and epithelial cells) include *Streptococcus sanguis, S. oralis* and *Gamella morbillorum*. The *B. loeschei* streptococcal-specific adhesin of the present invention is a basic protein with an isoelectric point (pI) of 7.4–8.4 composed of six 75 kD subunits so as to have a native molecular mass of 450 kD. The N-terminal amino acid sequence is as follows:

ala-tyr-ser-his-val-lys-asn-ala-thr-gly-glu-asp-ileu-glu-arg   ileu-lys-glu-gly-asp-val-asp-asp-asp-ileu-glu-val-asn An amino acid analysis of the adhesin of the present invention provided the results summarized in Table 1 below.

TABLE 1

Amino Acid Analysis of the Surface Protein from *Bacteroides loeschei*

| Amino Acids | Residues per 100 Residues |
| --- | --- |
| Asparatate[1] | 10.8 |
| Glutamate[2] | 10.9 |
| Serine | 6.8 |
| Glycine | 8.0 |
| Histidine | 1.2 |
| Arginine | 3.9 |
| Threonine | 6.0 |
| Alanine | 9.0 |
| Proline | 4.7 |
| Tyrosine | 10.0 |
| Valine | 6.8 |
| Methionine | 2.4 |
| Isoleucine | 3.0 |
| Leucine | 7.2 |
| Phenylalanine | 3.6 |
| Lysine | 8.0 |
| Cystine | 0.4 |

[1]Residue may be either Asp or Asn.
[2]Residue may be either Glu or Gln.

The protein of the present invention was purified by a one step procedure which employed an anti-adhesin gG Sephraose 4B affinity column wherein both monoclonal and polyclonal antibody prepared against the adhesin worked satisfactorily. A more detailed description of this procedure is provided below in the Examples.

The purified, characterized protein in accordance with the present invention may be used in a method for inhibiting plaque formation in the oral cavity. When added to suspensions of streptococci and gamella possessing the appropriate carbohydrate receptor, the adhesin causes them to agglutinate thereby providing a mechanism for clearance from the oral cavity. In addition, the adhesin prevents other oral bacteria, which might ordinarily colonize the oral cavity by attaching to the streptococcal primary colonizers, from becoming established in the mouth. This group of bacteria includes strains of *B. loeschei, Veillonella atypica, Actinomyces viscosus, A. naesludii,* and other strains of *S. sanguis* and *S. mitis*. Removal of these secondary colonizing bacteria advantageously prevents the late colonizers from accreting to plaque deposits. The polyvalent effects of the protein are due to the fact that the various adhesins on the heterologous microbes recognize the same carbohydrate receptor on the primary colonizer. Thus, the protein, or a specific peptide (the binding site) derived from it, can prevent attachment and colonization of bacteria to hard and soft oral tissues by competing for common receptors. The mechanism of the adhesin is advantageous since it inhibits plaque formation in a very specific manner without disturbing the normal flora within the oral cavity.

In accordance with the method of the present invention, the adhesin, or an active peptide derived from it, may be used as a disinfectant, applied via an oral composition, such as a dentifris, mouthwash, toothpaste, etc. Alternatively, the adhesin or active peptide may be applied topically to plaque-prone areas of the teeth or gingivae. In this capacity, the adhesin functions in two distinct ways. First, the adhesin has the ability to agglutinate three different species of streptococci that are primary colonizers in the oral cavity allowing salivary flow to clear the complexes. Second, the adhesion can attach to primary colonizers already attached to teeth thereby preventing attachment of other gram positive and gram negative bacteria, including species of Streptococcus, Actinomyces, Bacteroides and Veillonella. In vitro testing showed that between 10 and 20 μg of adhesin was sufficient to block $10^8$ streptococcal cells completely in a volume of 200 ml and prevented them from interacting with the above mentioned heterologous strains of oral bacteria. In formulating oral compositions incorporating the adhesin in accordance with the present invention, the compositions may include conventional excipients or carriers in addition to the adhesin, such as excipients found in conventional dentrifices, mouthwashes, and toothpastes. Conventional ingredients include dilute alcohols, abrasives, glycerin, sodium benzoate, polysorbate, sodium borate and flavorings. It must be noted that an anionic detergent cannot be included in the oral composition since this ingredient may denature the protein or peptide. The concentration of the adhesin in the oral composition is generally in the range of 80 to 100 μg per ml volume of the composition (for all affected species of bacteria) and in the range of 50 to 80 ug per ml. In formulating the oral composition of the present invention, the pH may be acidic since the protein is stable to acid. For example, the pH may be in the range of about 3 to 7, more preferably in the range of about 3 to 5.5. The oral composition may be in the form of a dentifris, mouthwash, toothpaste, etc. so as to provide a means for delivering the adhesin to plaque-prone areas in the oral cavity.

In addition to the above oral composition and method of use employing the adhesin, antibodies prepared against the adhesin may be used in a diagnostic assay to detect the presence of species of *B. loeschei* in plaque or saliva as an indicator of gingivitis. Such an assay may be based generally on enzyme-linked immunosorbent assays (ELISAs). For example, a sample of plaque or scraping from the gingivae is placed into microtiter plate wells. The sample is first treated with purified monoclonal antibody, then treated with antimouse IgG conjugated to alkaline phosphatase and then developed with a phosphatase substrate. The adhesin may be bound to conventional markers, such as radiolabels. The protocol is based on the procedures outlined in Weiss et al, "Characterization of monoclonal antibodies ...," *Infect. Immun.*, January, 1988, pp. 219-224. For a sample of about 2 to 4 mg, the monoclonal antibody is used in the range of I to 10 µg. This diagnostic assay may also be in the form of a kit for detecting bacterial growth on teeth which includes the adhesin and a non-human erythrocyte.

In addition to the above-noted uses, the adhesin may also be employed as a diagnostic indicator for changes in the surface components of certain human tissues based on the adhesin's interactive properties with certain saccharide groups, such as GalNAc. This diagnostic procedure is essentially the same as the assay for gingivitis as described above. A tissue sample is immobilized on a slide or microtiter plate, and treated with the adhesin. The alkaline phosphate can be conjugated to the adhesin for a direct assay, or the "sandwich" technique may be employed by applying MAb after the adhesin and anti-mouse IgG (conjugated to alk. phosphatase) as described above with regard to the assay for gingivitis.

The adhesin from *B. loeschei* may also be used as a binding agent in a method for purifying GalNAc or lactose-containing polysaccharides of biological interest. In this procedure for purifying a desired polysaccharide, the adhesin can be conjugated to a carrier, such as CNBr-Sepharose 4B beads in the presence of GalNAc to protect the active site. The bead conjugate is placed into a small column, such as an affinity column, and the polysaccharide solution poured over it. The polysaccharide will bind to the column matrix and the contaminating material is washed out. The material bound to the column is released by washing the column with GalNAc or lactose and the sugars can be dialyzed away leaving only the purified polysaccharide.

EXAMPLES

Purification and Characterization of *B. loeschei* Adhesin

Bacterial strains and culture conditions. *Bacteroides loeschei* PK1295, *Streptococcus sanguis* 34, *Capnocytophaga ochracea* 25 and *Streptococcus sanguis* H1 were grown in screw cap tubes containing Schaedler broth (BBL, Cockeysville, Md.) at 37° C. under anaerobic conditions. Large scale cultures of *B. loeschei* were grown in 1-L bottles; 20 L of medium yielded roughly 40 g (wet weight) of cells. Cell pastes were stored at −20° C. until used.

Purification of the Streptococcal-Specific Adhesin. Affinity gels were prepared by activating 1 g of CNBr-Sepharose 4B (Pharmacia LKB, Sweden) and reacting it with 15 to 20 mg of MAb 5BB1-1 or 3AD6 (24) according to the manufacturer's instructions. The washed Sepharose beads bearing the coupled antibody were stored in 200 mM sodium borate buffer, pH 8.0, containing 0.8 percent NaCl (BBS) at 4° C. until used.

The adhesin was released from *B. loeschei* PK1295 by suspending 8 to 10 g of cells (wet weight) in 20 ml of BBS containing the protease inhibitors phenylmethyl sulfonyl fluoride (PMSF (5 mM)) and ethylenediamine tetracetic acid (EDTA (10 mM)) and subjecting the continuously cooled cell suspension to ultrasonic disruption with a Branson model 350 sonifer (Heat Systems, Plainsview, N.Y.) operating at 70 percent of maximum power output for 4 minutes. Unbroken cells and membrane fragments were removed by centrifugation at 240,000×g for 60 minutes in a Sorval model ADT75B ultracentrifuge (Dupont, Newton, Conn.). The supernatant was concentrated to a volume of 4 to 5 ml in an Amicon filtration unit (Amicon, Danvers, Mass.) equipped with a YM-10 low protein binding membrane and the concentrate was added to a vial containing 300 mg of the MAb conjugated beads. The suspension containing beads and sonic concentrate was mixed by end-over-end rotation for 14 hours at 4° C. After mixing, the beads were separated from the concentrate by low speed centrifugation, 4000×g for 3 minutes and the concentrate was saved for further analysis to determine whether all of the adhesin had been removed. The Sepharose beads carrying the immune complex, MAb and adhesin, were rinsed once with 3 ml of BBS containing protease inhibitors, three times with 3 ml of BBS containing protease inhibitors plus 2 mM (3-(3-cholamidopropyl)-dimethylammonio)-1-propane sulfonate (CHAPS), once with 3 ml of BBS containing 2 mM CHAPS plus 1M NaCl, twice with 3 ml of BBS containing 2 mM CHAPS and six times with 3 ml of 20 mM (Tris (hydroxymethyl) aminomethane) buffer (Tris-HCl), pH 8.0 to remove contaminating adherent material. Adhesin was eluted by treating the beads three times with 3 ml of 5 percent acetic acid. Acetic acid washes were concentrated to a volume of 0.5 to 1 ml by centricon filtration (Amicon, Danvers, Mass.). The pH of the solution was then increased to 4.6 by several passages of the adhesin solution through the concentrating filter replacing the lost volume with 50 mM sodium acetate buffer, pH 4.6 containing 0.02 percent azide. This procedure yielded between 200 to 300 ug adhesin protein. In some instances, the pH of the adhesin solution was raised to 6.8 by the addition of NaOH and 0.1M Tris-HCl buffer, pH 6.8. The adhesin was stored at −20° C.

The efficiency of the recovery was estimated by resolving samples of the purified adhesin, supernatant fluid following adsorption to the affinity beads and the pellet of the centrifuged ultrasonic sample on SDS gels, immunobloting the separated polypeptides and developing the nitrocellulose filters with the appropriate antibody-conjugate system (see below). Scanning the intensity of the stains on dried gels with an Ultroscan XL laser densitometer (LKB, Uppsala, Sweden) and calculating the area under the peaks indicated that between 85 and 90% of the adhesin had been recovered by the MAb affinity matrix. Assuming that *B. loeschei* is similar to other gram negative bacteria, water comprises 70% of the cells' dry weight and 55% of the dry weight is protein. Thus, of a 10 g (wet weight) cell pellet, 1.65 g is protein. With a yield of 300 µg of adhesin protein, the adhesin represents roughly 0.02% (300 ug/$1.65 \times 10^6$ µg×100) of the cell's total protein. Protein concentration was determined by the commercially available BioRad protein assay kit (BioRad Labs, Richmond, Calif.).

Preparation of Rabbit Polyclonal Anti-Adhesin Antibody. After withdrawing a 30 ml sample of blood, a four month old white, female New Zealand rabbit was given three intradermal injections consisting of a total of 150 μg of the streptococcal-specific adhesin emulsified in ml Ribi adjuvant (Ribi Immunological Research, Hamilton, Mont.) over a period of 6 weeks. Blood was subsequently withdrawn from the central ear artery of the immunized rabbit, allowed to clot overnight and the serum was stored at −20° C. until used. Rabbit IgG was purified by a two step procedure employing ammonium sulfate precipitation and DEAE ion exchange chromatography. The IgG was ultimately made up in 0.02M phosphate buffer, pH 7.2 containing 0.78 percent NaCl (PBS) and stored at −20° C. until needed.

Coaggregation Inhibition and Hemagglutination Tests. Quantitative coaggregation experiments were performed using the spectrophotometric procedure of McIntire et al ("Mechanism of coaggregation between *Actinomyces viscosus* T14V and *Streptococcus sanguis* 34," *Infect. Immun.*, 21, pp. 978–988 (1978)). Inhibition of coaggregation studies with anti-streptococcal specific adhesin serum were performed as follows. A series of test tubes containing a suspension of $10^9$ *B. loeschei* cells in coaggregation buffer (CAB (0.001M Tris-HCl, pH 7.4; 0.15M NaCl; 0.0001M CaCl; 0.0001M MgCl$_2$ and 0.002% NaN$_3$)) received anti-adhesin IgG (in PBS) in the range of 98 to 200 μg of protein to a volume of 400 μl. The mixture was incubated at room temperature with constant shaking for 30 minutes. After the incubation period, 200 μl of a suspension of *S. sanguis* 34 ($10^9$ cells) was added to each tube to a final volume of 600 ul, the tubes were mixed vigorously for 5 minutes and the tubes were centrifuged for 1 minute at 500×g. The supernatants were diluted 1:2 with CAB and optical density at 600 nm was measured with a Gilford model 2400 spectrophotometer (Gilford, Oberlin, Ohio). Controls consisted of mixture of both suspensions containing PBS instead of IgG or 200 μl suspensions of each organism brought to a volume of 600 μl with CAB. The percent inhibition of coaggregation was determined using the procedure of McIntire et al.

Qualitative studies using the purified adhesin as the inhibitor were performed as follows. A suspension of $2.5 \times 10^8$ *S. sanguis* cells (50 μl) in CAB and adjusted to a pH of 5.0 with acetate buffer was incubated with 2.75 to 22 μg of adhesin protein at room temperature. After gentle agitation for 30 minutes, $5 \times 10^8$ *B. loeschei* cells were added to the mixture and shaken for several minutes until the control assay without adhesin added showed strong coaggregation. If the pH of the adhesin solution and the streptococcal cell suspension had been adjusted to 6.8 or greater, the cells quickly aggregated after mixing. The assays were scored visually assigning values between 0 to +4 or the results were recorded photographically. To establish the specificity of the purified adhesin, controls were performed using the coaggregation pair *S. sanguis* H1 and *C. ochracea* 25. These assays were performed as described above.

Hemagglutination studies were carried out with sheep erythrocytes (RBCs) stored in Alsevers solution. RBCs were washed three times in Hank's buffered saline solution and packed cells were diluted 1:5 in phosphate buffered saline (PBS). One ml of RBCs was treated with 10 μl of clostridial type X neuraminidase (Sigma Chemical Co., St. Louis, Mo.) containing 10 units per ml PBS for 1 hour at 37° C. RBCs were washed twice in PBS containing 0.1% bovine serum albumin and 0.02% sodium azide and adjusted to a density of $5 \times 10^9$ cells per ml in the same buffer. Hemagglutination assays were performed in microtiter plates; each well contained 80 μl of neuraminidase treated or untreated RBCs and between 2.5 to 16 μg purified adhesin (pH 6.8) in a final volume of 140 μl. Controls consisted of untreated cells plus adhesin or treated cells containing buffer only. Where required, the galactosides, N-acetyl-D-galactosamine, D-glucosamine, D-galactose and lactose were added to a final concentration of between 6 and 25 mM. The microtiter plates were incubated at room temperature with vigorous mixing for 30 minutes. Plates were then centrifuged and the size and nature of the resultant pellets were scored visually and photographed. The same protocol was used to test for agglutination of suspensions of *S. sanguis* 34 or *S. sanguis* H1. Suspensions containing $5 \times 10^8$ cells (in 25 mM sodium acetate, pH 5.6) were incubated with between 5 and 10 μg of adhesin protein with mixing at ambient temperature. When required, the galactosides described above were added to the agglutination assay at levels of between 6 and 25 mM.

Polyacrylamide Gel Electrophoresis and Isoelectric Focusing. Native anionic PAGE was carried out on 14×13 cm, 7 percent polyacrylamide gel slabs using the Tris-HCl glycine buffering system of Davis ("Disc electrophoresis. II. Method and application to human serum," *Ann. N.Y. Acad.*, 12, pp. 404–427 (1964)); between 0.5 and 8 μg of protein were added to the sample wells. Denaturing gel electrophoresis was carried out according to the method of King and Laemmli ("Polypeptides of tail fibers of bacteriophage T4", *J. Mol. Biol.*, 62, pp. 465–477 (1971)); similar protein loads were added to the sample wells. Bands on the gels were visualized with Coomassie blue R250 stain in accordance with the King and Laemmli method.

Isoelectric focusing was performed on commercially available pH 3 to 10 ampholine-containing polyacrylamide slabs according to the manufacturers instructions (Novex Corp., Encinitas, Calif.). Samples containing between 2 and 10 μg of adhesin and a solution containing proteins with known isoelectric points (cytochrome C (pI=9.6), chymotrypsin (pI=7.0), whale myoglobin (pI=8.05), equine myoglobin (pI=7.0), human carbonic anhydrase (pI=6.5), bovine carbonic anhydrase (pI=6.0), lactoglobulin B (pI=5.1) and phycocyanin (pI=4.65)) were run concomitantly on the gels. The solution of standard proteins was used to determine the linearity of the pH gradient in the gel and, following staining, the position of the adhesin on the gel was used to estimate its pI.

The native molecular weight of the adhesin was estimated by anionic gradient (3 to 20 percent) gel electrophoresis according to the method of Lambin and Fine ("Molecular weight estimations of proteins by electrophoresis in linear polyacrylamide gradient gels in the absence of denaturing agents," *Anal. Biochem.*, 98, pp. 160–168 (1979)). Oligomeric and monomeric forms of apoferritin ($M_r$=886,000 and 443,000), urease ($M_r$=545,000 and 272,000) and bovine serum albumin ($M_r$=132,000 and 66,000) served as molecular weight standards.

Immunoblot analyses were performed by separating adhesin polypeptide(s) SDS gel, transferring the protein components to nitrocellulose filters, treating the filters with 1:1000 dilutions of MAb 3AD6 IgG (3 mg/ml) or 1:2000 dilutions of polyclonal IgG (5 mg/ml) and visualizing the immune complex with a commercially available alkaline phosphatase goat anti-mouse IgG conjugated secondary antibody and dye indicator system (Promega, Madison, Wis.).

N-terminal Amino Acid Sequencing of the Adhesin. Lyophilized samples containing between 0.5 and 1 nmoles of adhesin were dissolved in 1 percent trifluoroacetic acid and processed by automated Edman degradations using a Model 470A gas phase sequencer (Applied Biosystems, Foster City, Calif.) in conjunction with the standard "NoVac" program supplied by the manufacturer. Phenylthiohydantoin derivatives were identified by HPLC on an IBM cyano column. The system used with this column consisted of a Perkin Elmer Series 4 liquid chromatograph, a LC-85B spectrophotometric detector and a LCI 100 computing integrator. These procedures were performed under contract with the University of California, San Diego.

Amino Acid Analysis of the Adhesin. Approximately 2 nmole of adhesin was hydrolyzed with constant boiling 6N HCL at 110° C. for 16 or 24 hours. The dried residue was dissolved in Beckman sample buffer diluent and analyzed with a Beckman Gold System HPLC amino acid analyzer using ninhydrin postcolumn derivatization as the detection system. Amino acid standards were obtained from Beckman.

RESULTS

Purification of the B. loeschei Streptococcal-Specific Adhesin.

FIG. 1 is a demonstration of the purity of the streptococcal-specific adhesin by immunoblot analysis, denaturing and native anionic gel electrophoresis. Lanes A–C are denaturing SDS gel. Lane A, 2 µg purified adhesin. Lane B contains the following molecular weight standards (top to bottom); phosphorylase A, ($M_r$=97,400); bovine serum albumin, ($M_r$=66,200); ovalbumin ($M_r$=42,700), carbonic anhydrase ($M_r$=31,000), trypsin inhibitor ($M_r$=21,400), lysozyme ($M_r$=14,400). Lane C contains the following molecular weight standards (top to bottom); myosin, ($M_r$=200,000), β-galactosidase, ($M_r$=116,500), phosphorylase A, bovine serum albumin and ovalbumin. Lane D, immunoblot developed with MAb 3AD6, 0.5 µg adhesin run in gel. Lane E, immunoblot developed with rabbit polyclonal anti-adhesin, 0.5 µg adhesin run in gel. Lane F, 6 µg adhesin resolved in a native anionic gel (positive electrode at bottom). The batchwise purification of the adhesin with the MAb 5BB1-2 or 3AD6 conjugated to a Sepharose 4B matrix yielded preparations that were greater than 95% pure as determined by scanning laser densitometry of native (FIG. 1, lane F) and denaturing (FIG. 1, lane A) gel electrophoretograms. The minor contaminants which migrated more rapidly than the adhesin monomer, $M_r$=75,000, (FIG. 1, lane D and E) reacted with the MAb or polyclonal antiserum specific for the adhesin (FIG. 1, lane C) suggesting that some small fraction of the native protein was slightly degraded during the purification procedure. These large fragments of the molecule must have retained the epitope(s) recognized by MAb 5BB1-2 and 3AD6 since they remained associated with the affinity matrix during the purification process and reacted with other MAbs (i.e. 5DB5 and 3BC5) capable of visualizing the adhesin on immunoblots. On native anionic polyacrylamide gels (FIG. 1, lane F), the adhesin migrated as a single band remaining near the top of the gel. The relatively slow migration rate in the electrical field was the first suggestion that the adhesin was a basic protein possessing a net positive charge. The protein exhibited the property of aggregating at a pH above neutrality. If the pH of the protein solution was increased to between 7.5 and 8.0, the protein precipitated out of solution and could not be solubilized by making the suspension acid (pH 3) or by treatment with either 6M urea or 4% SDS.

Figure 3:
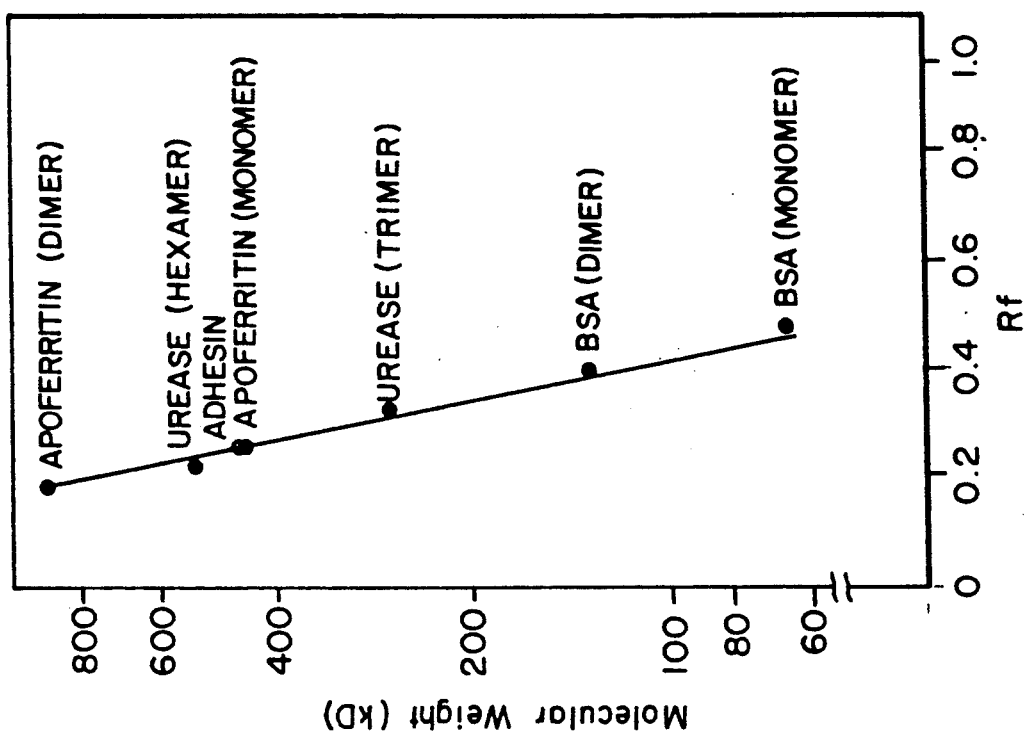
FIG. 3 is a graph showing the pH gradient of the streptococcal-specific adhesin.
Figure 2:
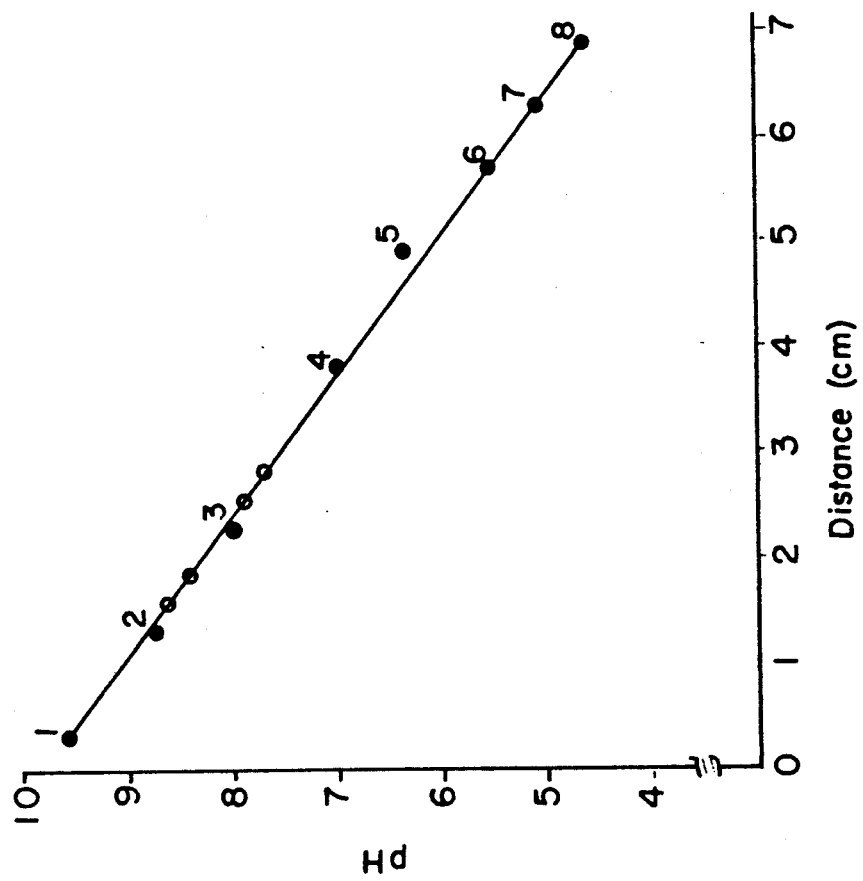
FIG. 2 is a graph showing an estimation of the native molecular weight of the streptococcal-specific adhesin.

Properties of the Adhesin. The native molecular weight of the adhesin was estimated by comparing the migration rate of the protein on 3 to 20 percent gradient anionic polyacrylamide gels with monomeric and polymeric forms of reference proteins. FIG. 2 is an estimation of native molecular weight of the streptococcal-specific adhesin by anionic gradient gel electrophoresis. The open circle denotes the relative position of the adhesin in the gel. FIG. 2 shows that the adhesin migrates like a protein with a $M_r$=450,000. Thus, in its native form, the adhesin appears to exist as a hexamer. The pI of the adhesin was determined by isoelectric focusing. FIG. 3 shows a distribution of the streptococcal-specific adhesin in a pH gradient. Standards (closed circles) are (1) cytochrome C, (2) a-chymotrypsin, (3) whale myoglobin, (4) equine myoglobin, (5) human carbonic anhydrase, (6) bovine carbonic anhydrase, (7) b-lactoglobin B and (8) phycocyanin. The open circles indicate the positions of the adhesin bands (6 µg added, bands of near-equal intensity). FIG. 3 shows that the affinity purified adhesin preparations migrated in an apparent polydispersed fashion over a pH range of 7.4 to 8.4. The pI of the adhesin in crude preparations was determined by transferring the proteins to nitrocellulose filters; the adhesin was visualized by immunoblot staining. The latter preparations appeared to be less polydispersed and exhibited a pI of between 8.2 and 8.7. Thus, the autoagglutination observed as the pH of the adhesin solution rises above neutrality probably reflects the protein-protein interactions that occur among the adhesin molecules as they approach their pI.

N-terminal amino acid sequencing identified the initial 28 amino acids of the mature protein; this portion of the adhesin was shown to consist of the following amino acid residues:

ala-tyr-ser-his-val-lys-asn-ala-thr-gly-glu-asp-ileu-glu-arg-ileu-lys-glu-glu-asp-val-asp-asp-asp-ileu-glu-val-asn The sequenced segment of the adhesin contains a relatively large number of charged amino acids including 6 aspartate residues. In contrast to the proteins overall basic character, 10 of the N-terminal charged amino acids are acidic in nature. Of the 28 amino acids, only one (tyr) is strongly hydrophobic. The results of an amino acid analysis of the protein adhesin are summarized in Table 1 above. Glx and Asx account for 22 percent of the protein's amino acid residues while basic amino acids (arg, his and lys) constitute 13 percent of the total residues. A significant number of the potentially acidic amino acid residues, i.e. asx and glx, probably exist as asn or gln since the pI of the adhesin ranges between 7.4 and 8.4.

Figure 4:
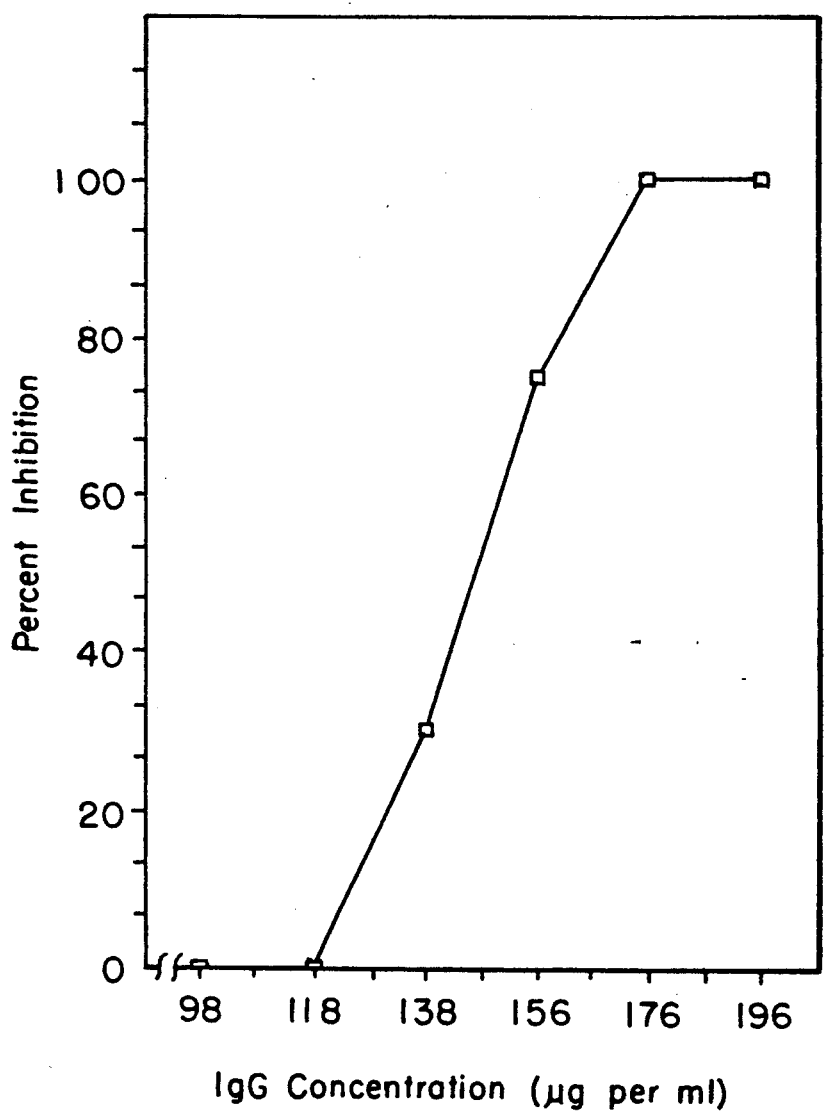
FIG. 4 is a graph showing the inhibition of coaggregation by preincubation of *B. loeschei* cells with polyclonal anti-adhesin prior to adding *S. sanguis* cells.

Coaggregation Inhibition Studies. To establish that the purified protein was indeed the streptococcal specific adhesin, an anti-adhesin polyclonal antiserum was produced in rabbits and its ability to inhibit coaggregation between B. loeschei and S. sanguis was determined. Since the MAbs originally prepared against the adhesin were potent inhibitors of coaggregation and erythrocyte agglutination by B. loeschei, it was reasoned that the polyclonal antiserum would duplicate, at least in part, the action of the MAbs. FIG. 4 is a graph showing the inhibition of coaggregation by preincubation of *B. loeschei* cells with polyclonal anti-adhesin prior to adding *S. sanguis* cells. A preimmune IgG preparation was not inhibitory up to a concentration of 1 mg ml$^{-1}$. FIG. 4 shows that the purified IgG fraction of the antiserum inhibited the interactions, however, it was not as effective as the MAbs which inhibited coaggregation in the range of 0.5 to 5 ug antibody protein. IgG prepared from preimmune serum had no effect on the coaggregation reaction at levels of 1 mg protein ml$^{-1}$. At similar concentrations (between 98 and 200 μg IgG protein), the polyclonal antiserum also inhibited hemagglutination of sheep RBCs by cell suspensions of *B. loeschei*. In addition, the purified polyclonal IgG reacted with purified preparations of adhesin in a fashion identical to the MAbs on immunoblots (FIG. 1, lane E). The IgG of the polyclonal antiserum functionally resembled the MAbs in that it did not agglutinate *B. loeschei* cells nor did it produce precipitin reactions with crude or purified adhesin preparation in immunodiffusion plates.

Figure 5:
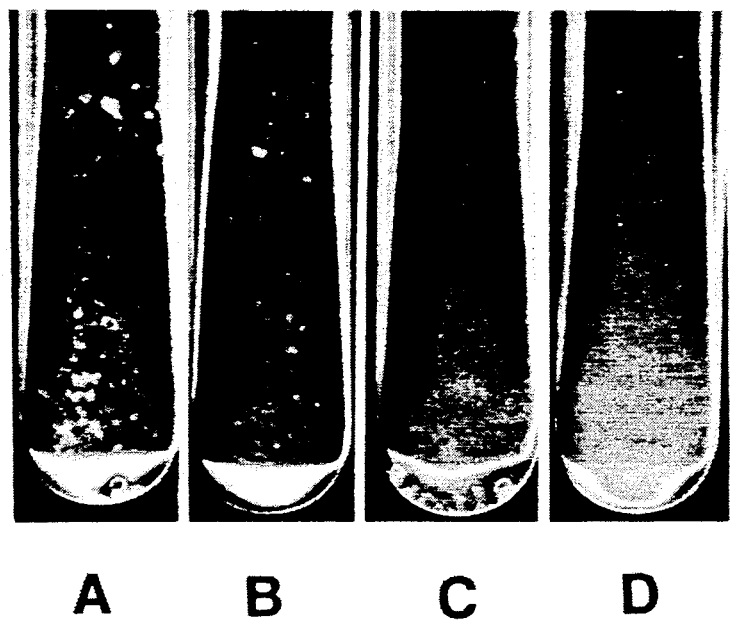
FIG. 5 is a picture showing reaction mixtures indicating the inhibition of coaggregation between *B. loeschei* and *S. sanguis;*

The purified adhesin itself was capable of inhibiting coaggregation at an acid pH (4.6) when preincubated with *S. sanguis* cells prior to the addition of *B. loeschei* cells. FIG. 5 shows the inhibition of coaggregation between *B. loeschei* and *S. sanguis* by preincubating *S. sanguis* cells with streptococcal-specific adhesin. All reaction mixtures contain $5 \times 10^8$ *S. sanguis* cells. Panel A, control; panel B, 5.5 μg adhesin added; panel C, 11 μg adhesin added; panel D, 22 μg adhesin added. Concentrations between 11 and 22 ug (equivalent to 0.2–0.4 μM native protein) of adhesin protein completely inhibited coaggregation between these two microorganisms (FIG. 5, panels C and D). However, constant mixing of the cell suspension containing 11 ug of adhesin protein (FIG. 5, panel C) eventually allowed some aggregation to occur after 30 minutes (approximately 25 percent of the control (A) as estimated visually); at 22 μg, no coaggregation was observed after an overnight incubation. Since the concentration of cells used in the assay was known and since blocking occurred in levels between 11 and 22 μg of adhesin, a rough approximation of the number of adhesin molecules required to block each streptococcal cell was determined. An estimated 5.6 to $11 \times 10^5$ molecules per cell resulted in complete abolition of coaggregation. To establish that the effect of the adhesin preparation on coaggregation was specific and not result of electrostatic interactions between the basic protein and streptococcal cells, a suspension of *S. sanguis* H1 was incubated with 22 μg of adhesin prior to addition of its partner cell, *C. ochracea* strain 25 (26). The adhesin had no effect on the coaggregation reaction.

Figure 6:
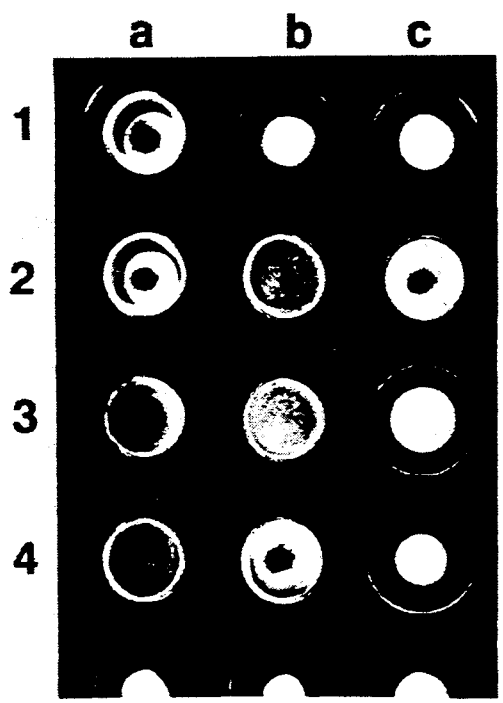
FIG. 6 is a photograph indicating the hemagglutination of neuraminidase-treated sheep erythrocytes by the purified adhesin.

FIG. 6 indicates hemagglutination of neuraminidase-treated sheep erythrocytes by the purified adhesin. Each well contained $5 \times 10^7$ cells. Column A, line 1 (control), untreated sheep RBCs plus 11 μg adhesin; column A, line 2 (control) treated sheep RBCs plus PBS buffer; column A, line 3; treated RBCs plus 2.75 μg adhesin; column A, line 4, treated RBCs plus 5.5 μg adhesin; column B, line 2, treated RBCs plus 11 μg adhesin; column B, line 3, treated RBCs plus 16.5 μg adhesin; column B, line 4, treated RBCs preincubated with 6 mM N-acetyl-D-galactosamine plus 11 μg adhesin; column C, line 2, (control) treated RBCs plus 40 μl acetate buffer. In contrast to the experiment described above, addition of similar levels of purified adhesin preparations (5–10 ug (equivalent to a concentration of 0.1–0.2 μM of native adhesin)) to neuraminidase-treated RBCs resulted in their rapid agglutination (FIG. 6, column B, lines 2 and 3). However, it is important to note here that these experiments were carried out at a pH of 6.8 with the adhesin being diluted in PBS prior to mixing with the RBCs. No immediate hemagglutination was observed with untreated erythrocytes, but with prolonged incubation (30 to 60 minutes at RT), a slight formation of particulate material was noted in the reaction mixture (FIG. 6, column A, line 1). Adding N-acetyl-D-galactosamine at a final concentration of 6 mM to the erythrocytes prior to introducing adhesin prevented hemagglutination (FIG. 6, column B, line 4). At concentrations of 10 to 25 mM, galactosamine, lactose and galactose also inhibited agglutination.

Figure 7:
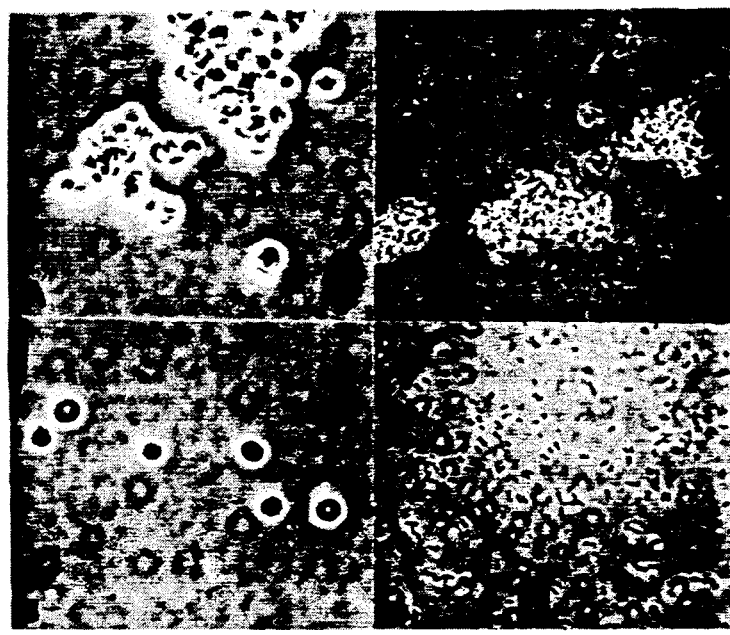
FIG. 7 is a series of photomicrographs of adhesin mediated hemagglutination of sheep RBCs and aggregation of the *S. sanguis* 34 cells.
Figure 8:
FIG. 8 is a photo showing the specificity of the adhesin-mediate aggregation of streptococcal cells.

FIG. 7 shows photomicrographs of adhesin mediated hemagglutination of sheep RBCs and aggregation of the *S. sanguis* 34 cells. A. Sheep RBCs plus 20 μg adhesin protein, B. RBC control (untreated RBCs plus 20 μg adhesin), C. streptococcal cells plus 10 μg adhesin protein and D. streptococci control (cells in buffer only). Magnification is 480×. These photomicrographs of reaction mixtures containing adhesin demonstrate conclusively that the adhesin mediated extensive agglutination of the neuraminidase-treated RBCs (FIG. 7, panel A), the adhesin had no effect on untreated RBCs (FIG. 7, panel B). If an aliquot of the neutral adhesin solution (5 μg protein) was added to *S. sanguis* 34 cells suspended in PBS, the streptococci agglutinated immediately upon mixing (FIG. 7C). The appearance of the suspension was identical to that seen in conventional coaggregation experiments (see FIG. 5, panel A); photomicrography revealed that, like the RBCs, the streptococcal cells had undergone extensive aggregation (FIG. 7, panel C). In the controls, adjusted to a Ph of 6.8, no aggregation occurred in the absence of adhesin (FIG. 7, panels B and D). Like the RBCs, addition of the galactosides in the same concentration range inhibited or reversed the adhesin mediated aggregation. FIG. 8 shows the specificity of the adhesin-mediate aggregation of streptococcal cells. A. *S. sanguis* 34 ($5 \times 10^8$ cells ml$^{-1}$) plus 10 ug adhesin protein. B. *S. sanguis* H1 ($5 \times 10^8$ cells per ml) plus 10 μg adhesin protein. Incubated for 5 minutes at ambient temperature with mixing. FIG. 8 shows that ten micrograms of adhesin failed to aggregate a cell suspension of *S. sanguis* H1, a strain closely related to *S. sanguis* 34, indicating that the interaction was specific for a receptor on the latter.

The lectin-like protein on the surface of *B. loeschei* that mediates coaggregation with *S. sanguis* and hemagglutination with a wide variety of erythrocytes is one of the few bacterial adhesins to be purified in any significant quantity and partially characterized with regard to both structure and function. The adhesin was related from cells by ultrasonic disruption and purified to electrophoretic homogeneity by affinity chromatography. From the adhesin's amino acid composition and pI, it appears to be a hydrophilic protein with a comparatively strong positive charge. In its native state, the adhesin exist as a relatively large hexameric molecule with an estimated $M_r$ of 450,000. The unequivocal identification of the adhesin's 28 amino terminus residues suggests that this region of the six monomers comprising the native protein is homologous. However, the amino acid sequence of the remainder of the monomer may not be so highly conserved since isoelectric focusing data indicated that the protein migrates as 4 distinct bands. The apparent polydispersed nature of the purified preparation may reflect posttranslational modifications of the adhesin monomers or it may be a result of acid hydrolysis of the amide groups in glutamine and asparagine during purification. A comparison of N-terminal amino acid sequences of the *E. coli* type 1, P and bacteroides adhesin showed that each of the *E. coli* proteins matched with the *B. loeschei* protein at two or four non-consecutive positions (FIG. 9), respectively; the two enteric adhesins only showed six non-consecutive cross-matches. Thus, there appears to be little or no homology in this portion of the three proteins.

It was essential to establish that the protein of $M_r = 450,000$ associated with the *B. loeschei* fimbriae was the adhesin because the distinction between the adhesin and fimbrillin or pilin subunits in other systems had not been clearly delineated in many earlier studies. The following evidence supported the conclusion that the purified protein was the adhesin; (a) the polyclonal antiserum prepared against the adhesin inhibited both coaggregation and hemagglutination, (b) the purified adhesin itself inhibited coaggregation with streptococcal cells at an acid pH or agglutinated neuraminidase-treated erythrocytes and streptococci at a neutral pH, and (c) electron micrographs of purified adhesin preparations shows no fimbrial structures. The coaggregation inhibition studies established that the adhesin readily binds to partner cells in relatively large numbers. Rough estimates indicated that each cell may bind as many as $4 \times 10^5$ adhesin molecules. This number is approximately three orders of magnitude greater than the value obtained for the number of adhesin molecules found on individual *B. loeschei*. It is clear that the adhesin recognizes the same sugars on the procaryote and eucaryote receptors since the same set of galactosides inhibit blocking of coaggregation and agglutination of streptococcal cells and RBCs. However, the nature of those receptors is most probably very different. The bacterial receptor may be similar to the *S. sanguis* 34 N-acetyl-D-galactosamine and galactose-containing cell wall polysaccharide that an adhesin *Actinomyces viscosus* T14V recognizes, while the erythrocyte receptor is apt to be a glycoprotein or glycolipid. *S. sanguis* H1, which failed to interact with the adhesin and, thus, served as an aggregation control, possesses a polysaccharide receptor that is structurally distinct from that described in strain 34.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed:

1. A purified, characterized surface protein from *Bacteroides loeschei* having a molecular mass of about 450 kD and an N-terminal amino acid sequence as follows:

ala-tyr-ser-his-val-lys-asn-ala-thr-gly-glu-asp-ileu-glu-arg-ileu-lys-glu-gly-asp-val-asp-asp-asp-ileu-glu-val-asn.

2. A method for inhibiting plaque formation in the oral cavity of a host which comprises administering to the host an effective amount of a purified, characterized surface protein from *Bacteroides loeschei* having a molecular mass of about 450 kD and an N-terminal amino acid sequence as follows:

ala-tyr-ser-his-val-lys-asn-ala-thr-gly-glu-asp-ileu-glu-arg-ileu-lys-glu-gly-asp-val-asp-asp-asp-ileu-glu-val-asn.

3. An oral composition for inhibiting plaque formation which comprises in an orally acceptable excipient an effective amount of a purified, characterized surface protein from *Bacteroides loeschei* having a molecular mass of about 450 kD and an N-terminal amino acid sequence as follows:

ala-try-ser-his-val-lys-asn-ala-thr-gly-glu-asp-ileu-glu-arg-ileu-lys-glu-gly-asp-val-asp-asp-asp-ileu-glu-val-asn.

4. A composition of matter comprising a protein of claim 1 bound to a radiolabel marker.

5. A mouthwash composition comprising an effective amount of the protein of claim 1, water and mouthwash excipients.

6. A dentifrice composition comprising an effective amount of the protein of claim 1 and a polishing agent.

* * * * *